United States Patent [19]

Driscoll et al.

[11] 4,115,537
[45] Sep. 19, 1978

[54] RESIN TABLET AND USE THEREOF IN DIAGNOSTIC TESTS

[75] Inventors: Richard C. Driscoll; Clara B. Morejon, both of Miami, Fla.

[73] Assignee: American Hospital Supply Corporation, Evanston, Ill.

[21] Appl. No.: 720,990

[22] Filed: Sep. 7, 1976

[51] Int. Cl.² .................. G01N 33/16; A61K 43/00; C08L 1/00
[52] U.S. Cl. ........................ 424/1; 23/230.6; 252/408; 260/17.4 CL; 424/14
[58] Field of Search .............. 252/408; 424/1, 14, 424/19; 260/17.4 CL, 17.4 ST; 23/230 B, 230.6

[56] References Cited

U.S. PATENT DOCUMENTS

| | | | |
|---|---|---|---|
| 3,826,767 | 7/1974 | Hoover et al. | 260/17.4 ST |
| 3,994,843 | 11/1976 | Hickey | 260/17.4 CL |
| 4,015,939 | 4/1977 | Lewin et al. | 23/230 B |
| 4,016,117 | 4/1977 | Griffin | 260/17.4 ST |

Primary Examiner—Richard E. Schafer
Assistant Examiner—Christine M. Nucker
Attorney, Agent, or Firm—Tilton, Fallon, Lungmus & Chestnut

[57] ABSTRACT

Resilient polystyrene anion-exchange resin beads in a size range of 50 to 600 mesh are bound together by microcrystalline cellulose to form a tablet suitable for use in conducting clinical diagnostic tests, and particularly, in making thyroxine determinations utilizing competitive protein-binding techniques.

23 Claims, No Drawings

RESIN TABLET AND USE THEREOF IN DIAGNOSTIC TESTS

BACKGROUND

A procedure for measuring total serum thyroxine by radioactive techniques was first developed by Ekins, as disclosed in Clin. Chim. Acta 5:453 (1960). In that procedure, which was termed "Saturation Analysis," extracted thyroxine (T4) was added to standard plasma solution containing radioactive iodine ($^{131}$I) labeled T4. Electrophoretic procedures were used to measure the shift of labeled T4 from globulin to albumin with the amount displaced being a measure of patient T4.

Murphy and Pattee (J. Clin. Endocrinol. 24:187 (1964)) describe a method of total serum thyroxine determination ("Competitive Protein Binding Analysis") similar to that of Ekins but technically simpler and more rapid. Bound T4 is released from the serum proteins by denaturation and precipitation with ethanol. This procedure leaves approximately 80 percent of the T4 in the alcoholic supernatant. After the supernatant is evaporated to dryness, a buffered reagent containing labeled T4, thyroxine binding globulin (TBG) and barbital is added to the extract. During a period of incubation, the extracted T4 competes with radioactive T4 for binding sites on the TBG. Thereafter, the solution is passed through a column of crosslinked dextran gel, or is exposed to anion-exchange resin beads, and the free thyroxine is bound to the gel or anion-exchange resin. The radioactive-labeled T4 bound to the gel, or to the resin beads, is proportional to the amount of T4 present in the original sample.

A more complete description of the prior art is set forth in U.S. Pat. Nos. 3,414,383 and 3,799,740, and in the references cited therein. The use of polystyrene anion-exchange resin beads to bind free T4 (both labeled and unlabeled) following an equilibrating step in which a solution of free extracted T4 from a sample of patient's serum competes with a known quantity of radioactive-labeled T4 bound to saturated TBG, is now common practice in clinical laboratories. Nevertheless, such beads do present problems and inconveniences both in production and in laboratory use. For example, even though such beads are relatively large (usually 35 mesh or larger), the weighing and handling of such beads are difficult whether performed in the laboratory or in a manufacturing facility. Keeping the beads together throughout a test may itself be a problem; should a single bead be lost during the performance of a test, the difference would significantly alter the results.

Furthermore, the use of conventional resin beads involves manipulative steps which are not only time consuming but, at least in some instances, increase the risks of bead loss. Thus, it has been generally considered necessary to carry out the competitive-binding equilibration step in advance of bead introduction, allowing such equilibration to take place in what amounts to an incubation step (usually at room temperature) over an interval of 5 to 15 minutes. Thereafter, the beads are introduced, intimately mixed with the fluid and again incubated for a similar interval. Two incubation periods are regarded as necessary; should the first incubation be omitted, reproducibility of test results is affected, apparently because the presence of large porous resin beads somehow interferes with or at least delays the development of equilibrium conditions during the competitive-binding step.

Following the equilibration step, the supernatant and the resin beads are separated and the radioactivity of one or the other (or both) is measured by means of a suitable gamma counter. However, before the actual measurement of radioactivity is taken, standard procedure requires that the resin beads be washed to remove residual TBG-bound thyroxine, again for the purpose of achieving reproducible results. Such a washing step is obviously time consuming, requires manipulative effort, and presents further possibilities for error. For example, should one or more beads be lost during the washing step, the test results might be seriously affected where the procedure involves measuring radioactivity from the resin; should less than all of the wash liquid be added to the supernatant, the accuracy of the results would again be jeopardized in a procedure where radioactive readings are taken from the supernatant.

While it has been suggested that the handling and measurement problems might be reduced if somehow the anion-exchange resin beads could be pressed into the form of a pellet or tablet, no such product is known to have become available in the past. The resilient porous nature of the polystyrene beads makes it virtually impossible to compress them to a stable compacted condition in which they will remain after the compressive force is removed. Binders (such as starch) are known but no binder systems for anion-exchange resin beads have been suggested which would permit tableting and at the same time would not interfere with proper functioning of the beads during a test procedure. Therefore, while certain of the advantages of tableting have been recognized, those advantages have not been realized in the past for anion-exchange resins, nor has there been any suggestion as to just how such advantages might be realized.

SUMMARY

One aspect of this invention lies in the discovery that an effective resin tablet for use in competitive binding tests and other clinical tests might be made from resilient polystyrene anion-exchange resin beads if such beads are of sufficiently small size and if a binder consisting essentially of microcrystalline cellulose is used. In addition to serving as a binder, the microcrystalline cellulose also functions as a disintegrant since the cellulose matrix swells upon contact with water to help disperse the resin beads. Unlike other binders such as starch, however, the microcrystalline cellulose does not form a gel and does not interfere with proper functioning of the beads or with effective equilibration during the competitive binding step.

Surprisingly, the use of microcrystalline cellulose as a binder-disintegrant also simplifies and shortens a competitive-binding thyroxine test because it eliminates the need for a bead-washing step and also eliminates the need for a pre-incubation step. Since pre-incubation — that is, a separate incubation step during equilibration — is rendered unnecessary, the equilibrating and separating steps may be performed substantially simultaneously. In other words, resin beads may be introduced before, during, or immediately following commencement of the competitive binding step. The result is a simplified procedure which not only saves time and effort but also reduces risks of manipulative error and misleading results.

Briefly, the product consists of a water-disintegratable tablet comprising a measured quantity of resilient porous beads of a particle size within the general range of 50 to 600 mesh, the beads being bound together by partices of microcrystalline cellulose and, at least in a preferred embodiment, by one or more other excipients. Alginic acid has been found particularly effective as a co-excipient. The beads themselves are standard, being typical (except for their relatively small size) of the type used in the past for similar diagnostic tests. Specifically, such beads are polystyrene-based, have strongly basic quaternary ammonium anion-exchange groups, and are both porous and resilient. A particularly effective bead composition has been found to be a styrene divinyl benzene polymer having quaternary ammonium exchange groups attached thereto and being in a chloride ionic form. A particle size range of 100 to 500 mesh is preferred, with 200 to 400 mesh being considered particularly effective.

As indicated, such a tablet not only facilitates production, handling, and laboratory use of the resin beads, but also results in improved competitive binding test procedures in which certain steps previously considered essential may now be eliminated. Thus, in a standard T4 test, or a compensated T4 test, where, in accordance with the teachings of the prior art, there are the steps of equilibrating a solution of free T4 extracted from a sample of patient's serum with a dilute buffered solution of a known amount of radioisotope-labeled T4 bound to saturated TBG, and of separating the unbound T4 with an anion-exchange resin, use of the tablet permits the equilibrating and separating steps to be performed concurrently, without pre-incubation of the solutions prior to introduction of the anion-exchange resin. Furthermore, following such combined steps, the beads may be separated from the supernatant simply by centrifugation and decantation, followed directly by measurement of radioactivity of either the supernatant or the beads. Specifically, no washing of the beads following decantation is required.

Other objects and advantages of the invention will become apparent as the specification proceeds.

DETAILED DESCRIPTION

Each resin tablet is composed of beads or particles of a polystryene-based anion-exchange resin such as, for example, a polystyrene divinyl benzene cross-linked resin marketed under the designation AG1-X4, or AG1-X8, by Bio-Rad Laboratories, Richmond, California. Such a resin has strongly basic quaternary ammonium exchange groups and, although other ionic forms would appear suitable, the chloride form is believed particularly effective. Such a resin, like other polystyrene-based ion-exchange resins, is resilient or spongy; although each bead may be compressed, it tends to return to its original shape when the compression force is removed, with the result that such a material would not normally be regarded as suitable for tableting, especially by direct compression methods. It is to be understood that the specific brand of exchange resin is given here only for purposes of illustration and that other ion-exchange resins having similar properties may be used, both the resins themselves and the tests in which they are used being known in the art.

Bead size is critical. Specifically, the resin beads should be of relatively small size, falling within the outside range of 50 to 600 mesh, or the preferred range of 100 to 500 mesh. Beads larger than 50 mesh cannot be used in a tablet of a size and binder content suitable for clinical diagnostic tests, and beads smaller than 600 mesh do not centrifuge properly. The optimum range is believed to be 200 to 400 mesh.

Microcrystalline cellulose is highly effective as a direct-compression binder for the resin tablet despite the resilience of the resin from which the particles or beads are formed. While the precise reasons for the effectiveness of microcrystalline cellulose as a binder for the resilient beads may not be fully known, it is believed that the relatively small size of those beads is significant. By reason of their small size, the resin beads provide relatively great surface area and binding capacity for their volume or mass. Thus, in the formulation of a tablet embodying this invention, adequate binding or ion exchange capacity may be achieved even though the resin beads constitute only 3 to 9 percent of the total weight of the tablet. The microcrystalline cellulose binder, which constitutes 90 to 96 percent by weight of the tablet, yields a product which is sufficiently hard and non-friable notwithstanding the resilience of the almost-microscopic beads carried in the binder matrix.

In a preferred formulation, each tablet also contains one or more additional excipients which serve as binders, disintegrants, and/or lubricants. Alginic acid is believed particularly effective as a secondary disintegrant. Like microcrystalline cellulose, alginic acid swells rapidly in the presence of water. Of particular importance is the fact that in a basic medium, at a pH level at which a typical T4 test would be run (about pH 8.6), alginic acid forms soluble salts which do not interfere with the test. Even at lower pH, such as pH 5.0 at which a typical T3 test might be run, any gel formed by alginic acid is so slight as to be inconsequential. Where alginic acid is included as an excipient in the tablet formulation, only a relatively small amount (1.0 to 5.0 percent by weight) should be used.

Other excipients may or may not be used which are more typical in tablet formulation. Thus, if a lubricant is required in connection with tablet formation, magnesium stearate may be included without adversely affecting the results of the diagnostic test. Where a lubricant such as magnesium stearate is desired, only a small amount, substantially less than 1.0 percent by weight, is ordinarily required.

While a variety of brands of microcrystalline cellulose are available and might be used, Avicel brand marketed by FMC Corporation, Marcus Hook, Pennsylvania, may be given by way of illustration as an effective dry binder material. The cellulose particles, although capable of swelling quickly in water, are insoluble in that medium. Because of the swelling action, the microcrystalline cellulose binder also acts as a disintegrant but, unlike commonly-used binder-disintegrants such as starch, the cellulose does not form a colloidal gel which would tend to entrap radioactive material and produce erroneous test results. In addition, the microcrystalline cellulose, after tablet disintegration and upon subsequent centrifugation, forms a densely-packed precipitate which occludes the radioactive supernatant, thereby producing highly effective test results without the resin-washing step ordinarily required in conventional thyroxine-measuring tests utilizing anion-exchange resins.

The tablet may be used in a variety of diagnostic tests requiring separation by means of an anion-exchange resin. For example, the tablet is useful in performing a standard T3 uptake test and, as already indicated, may be used in a standard T4 test, or a compensated T4 test of the type disclosed in U.S. Pat. No. 3,799,740. Both of the T4 tests, as previously known and described in the prior art, ordinarily involve the steps of equilibrating a solution of free T4, extracted from a sample of patient's serum, with a dilute solution containing a known quantity of radioactive-labeled T4 bound to saturated TBG, and thereafter separating, by means of the anion-exchange resin, the unbound T4 from the bound T4 in solution. The present process, utilizing a resin tablet, is essentially the same except that such steps may be formed substantially simultaneously, without pre-incubation of the equilibrating mixture prior to introduction of the ion-exchange resin, and that the final step of washing the beads, following centrifugation and decantation and prior to scintillation counting, is omitted. The result is a simplified test which may be performed with greater speed and efficiency, and with reduced risks of manipulative errors that might yield erroneous test results.

The following examples further illustrate the product and method of the invention.

EXAMPLE 1

Tablets in accordance with this invention may be produced by first spreading AG1-X8 resin, 200 to 400 mesh, in the wet condition in which it is available from the supplier (Bio-Rad Laboratories, Richmond, California) on a sheet of aluminum foil and drying 12 hours in an oven at 60° C. The resin is then allowed to equilibrate with a 22 percent humidity atmosphere for 24 hours. Thereafter, 30.00 grams of the dry resin are placed in a PK blender, equipped with an intensifier bar, along with 15.00 grams alginic acid (Kelco) and 403.75 grams microcrystalline cellulose (Avicel, as marketed by FMC). The dry ingredients are blended for one hour and then sieved through a 60 mesh screen, followed by 1.250 grams of magnesium stearate (Mallinckrodt). After further blending of the ingredients for 15 minutes, the dry mix is then tableted using a Stokes Mode "F" single punch tableting machine having shallow concave dies yielding 90 milligram tablets of one fourth inch in diameter. The batch formulation is sufficient for 5000 tablets each composed of 6.00 milligrams (mg) resin, 3.00 mg alginic acid, 80.75 mg microcrystalline cellulose, and 0.25 mg magnesium stearate. In actual practice, such formulation resulted in the production of 4400 tablets of excellent quality having a hardness of ca. 7 units (SC).

EXAMPLE 2

Comparative tests were conducted using the standard procedure set forth in data sheet CH45-DA (Rev. 12/74) published by Dade Division of American Hospital Supply Corporation, Miami, Fla. That procedure involved the following steps:

(1) Transfer 2.0 ml of T4 extraction reagent (anhydrous methyl alcohol) into 10-15 ml centrifuge tubes labeled Unknown, Control, Calibrators (previously called Standards) and Blank.

(2) Transfer, dropwise, 0.5 ml of the Unknown (serum), Control, and Calibrators into their respective tubes. To the Blank add 0.5 ml distilled water.

(3) Cover all tubes with paraffin film and mix on a vortex-type mixer for at least 30 seconds. Leave undisturbed at room temperature for 5 minutes.

(4) Centrifuge Unknowns and Controls for 5 minutes at approximately 900 rcf.

(5) Transfer 5 ml of $^{125}$I buffered thyroxine (warmed to room temperature) into the required number of plastic reaction tubes.

(6) Add 0.3 ml of the clear extract from each tube (Unknowns, Controls, Calibrators, and Blank) into properly marked tubes containing $^{125}$I buffered thyroxine.

(7) Cap tubes and mix gently until thoroughly mixed (e.g., hand inversion). Allow to stand for at least 10 minutes at room temperature (pre-incubation).

(8) Transfer ion-exchange resin to each of the reaction tubes. In one set of tests utilizing standard resin beads of 20-35 mesh, chloride form (AG1-X8), having quaternary ammonium exchange groups attached to a styrene divinyl benzene polymer lattice, a vial of beads was transferred to each reaction tube utilizing a funnel. In a parallel series of tests using tablets prepared in accordance with Example 1, a single tablet was simply placed in each reaction tube.

(9) Incubate by replacing caps on reaction tubes and rotating at room temperature (22-28° C.) for 15 minutes on any tube rotator which gives tumbling action.

(10) After incubation, tilt tubes to wash resin from caps.

(11) Insert a plunger gently into each tube to retain resin particles (and, in one series of tests, microcrystalline cellulose) within the tube while permitting the liquid to be poured off. The supernatant fluid is then poured off and discarded.

(12) Wash by carefully adding water down the stem of each plunger until all reaction tubes are about three-fourths full. Slowly move plunger up and down several times to wash the resin, ending with the plunger at the bottom of the tube. Discard liquid.

(13) Wash outside of tubes with water and wipe dry.

(14) Establish background count of gamma counter. Place each tube in well and count for one minute (CPM) or 10000 counts.

The following chart sets forth the comparative results of the two series of tests, such tests being identical as previously indicated except that in one series (Tablet Method) the tablets of Example 1 were used, whereas in the other series (Non-Tablet(Standard)Method) standard beads of 20-35 mesh were used:

| Samples | Tablet Method CPM | Results | Non-Tablet (Standard) Method CPM | Results |
|---|---|---|---|---|
| 0 | 21,498 | | 20,112 | |
| Calibrator 5 | 20,106 24,949 | | 20,353 25,562 | |
| Calibrator 10 | 25,483 30,754 | | 25,541 31,092 | |
| Calibrator 15 | 32,550 36,509 | | 30,635 34,740 | |
| Calibrator | 36,840 | | 34,607 | |
| RAC INTER | 28,848 28280 | 7.9 7.3 } 7.6 | 27,655 28,628 | 7.0 7.9 } 7.4 |
| RAC HIGH | 35,085 35,082 | 13.8 13.8 } 13.8 | 34,226 35,132 | 13.5 14.2 } 13.8 |
| No. 71 | 28,961 28,843 | 7.7 7.6 } 7.6 | 28,507 27,532 | 7.7 6.9 } 7.1 |
| No. 72 | 29,759 31,928 | 8.8 10.4 } 9.6 | 30,559 30,064 | 9.6 9.2 } 9.4 |
| No. 73 | 32,945 31,501 | 11.4 10.2 } 10.8 | 31,770 31,735 | 10.8 10.7 } 10.8 |

-continued

| | Tablet Method | | Non-Tablet (Standard) Method | |
|---|---|---|---|---|
| Samples | CPM | Results | CPM | Results |
| No. 74 | 26,680 | 5.7 ⎫ 6.3 | 27,139 | 6.4 ⎫ 6.3 |
| | 28,129 | 7.0 ⎭ | 26,878 | 6.2 ⎭ |
| No. 75 | 30,864 | 9.5 ⎫ 9.3 | | |
| | 30,414 | 9.2 ⎭ | 28,956 | 8.4 } 8.4 |
| No. 76 | 27,509 | 6.5 ⎫ 6.1 | 27,931 | 7.0 ⎫ 6.8 |

| | Formulation 1 | | Formulation 2 | |
|---|---|---|---|---|
| Sample | Original | 1 Wash | Original | 1 Wash |
| Cal .0 | 22577 | 21051 | 33243 | 32744 |
| Cal .0 | 22663 | 21630 | 33586 | 32364 |
| Cal .5 | 27561 | 26026 | 39504 | 38824 |
| Cal .5 | 27986 | 26620 | 39372 | 38939 |
| Cal .10 | 33722 | 32340 | 45564 | 44978 |
| Cal .10 | 33478 | 32433 | 45278 | 44539 |
| Cal .15 | 38946 | 38202 | 49245 | 48656 |
| Cal .15 | 38593 | 37474 | 48811 | 48663 |
| HC I | 31571 8.3 ⎫ 8.1 | 29809 7.8 ⎫ 7.8 | 43001 7.9 ⎫ 7.8 | 42642 8.3 ⎫ 8.1 |
| HOC I-150 | 31214 7.9 ⎭ | 29778 7.8 ⎭ | 42833 7.8 ⎭ | 42251 7.9 ⎭ |
| HC II | 38200 14.4 ⎫ 14.3 | 36880 14.3 ⎫ 14.3 | 49970 13.7 ⎫ 13.7 | 49571 14.1 ⎫ 14.4 |
| HOC 2-72 | 38054 14.2 ⎭ | 36856 14.3 ⎭ | 50204 13.7 ⎭ | 50157 14.6 ⎭ |

| | 26,765 | 5.7 ⎫ | 27,478 | 6.6 ⎫ | |
|---|---|---|---|---|---|
| No. 77 | 29,543 | 8.3 ⎬ 7.8 | 29,077 | 8.2 ⎬ 7.7 | |
| | 28,377 | 7.4 ⎭ | 28,241 | 7.3 ⎭ | |
| No. 78 | 27,061 | 6.0 ⎫ 6.4 | 26,726 | 6.1 ⎫ 6.2 | |
| | 27,865 | 6.7 ⎭ | 26,894 | 6.3 ⎭ | |
| Total Count 1 ml | 18,132 | | Total Count 1 ml | 17,723 | |
| Slope, %/ug | | 1.20 | | 1.18 | |

It is believed apparent that there is close agreement in the results obtained by the two procedures, and that the slopes are also similar.

EXAMPLE 3

Thyroxine levels in micrograms of thyroxine per deciliter ($\mu$g T4/dl) for 11 subjects were determined in accordance with the procedure of Example 2, using only resin tablets prepared in accordance with Example 1. Two tests were conducted for each subject: in Test A, the procedure as outlined in Example 2 was followed without alteration; in Test B, the same procedure was followed except that the 10 minute pre-incubation (step (7)) was omitted. The test results are as follows:

| Sample | Test A | Test B |
|---|---|---|
| Subject 1 | 7.8 | 7.9 |
| Subject 2 | 9.5 | 10.0 |
| Subject 3 | 10.3 | 10.3 |
| Subject 4 | 8.0 | 10.0 |
| Subject 5 | 8.2 | 8.7 |
| Subject 6 | 7.0 | 8.4 |
| Subject 7 | 8.4 | 9.6 |
| Subject 8 | 8.4 | 8.4 |
| Subject 9 | 0.7 | 1.4 |
| Subject 10 | 13.8 | 13.5 |
| Control 1 | 7.5 | 8.8 |
| Control 2 | 14.8 | 16.0 |

The data reveals no significant differences between the values of the serum samples and controls by both procedures, with and without the 10 minute pre-incubation step.

EXAMPLE 4

The procedure of Example 2, using only resin tablets, and modified to omit step (12), was carried out on several samples using two different formulations for the resin tablets. After the completion of each test procedure on each sample (i.e., after a radioactivity count was taken as set forth in step (14)), 5.0 ml of distilled water was added to each sample tube, the tube was capped, its contents mixed by inversion (two or three times), centrifuged, decanted, and recounted. The results, which indicate the effects of washing the solid material with 5.0 ml distilled water after each test was completed, are set forth below:

The assay values reveal no significant changes in $\mu$g T4/dl after one wash. The resin tablet formulations used in this test were as follows:

| Formulation 1 | |
|---|---|
| AG1-X8 Resin (200–400 mesh) dry | 6.00 mg |
| Alginic Acid | 3.00 mg |
| Avicel | 80.75 mg |
| Magnesium Stearate | 0.25 mg |
| Formulation 2 | |
| AG1-X8 Resin (200–400 mesh) dry | 8.00 mg |
| Avicel | 81.75 mg |
| Magnesium Stearate | 0.25 mg |

While in the foregoing we have disclosed embodiments of the invention in considerable detail for purposes of illustration, it will be understood by those skilled in the art that many of these details may be varied without departing from the spirit and scope of the invention.

We claim:

1. A water-disintegratable tablet for use in clinical diagnostic testing, comprising a predetermined quantity of resilient porous beads composed of polystryene-based anion-exchange resin having quaternary ammonium exchange groups and a particle size within the range of 50 to 600 mesh, said beads being bound together by a water-swellable binder composed essentially of microcrystalline cellulose.

2. The tablet of claim 1 in which the size range of said beads is 100 to 500 mesh.

3. The tablet of claim 2 in which the size range of said beads is 200 to 400 mesh.

4. The tablet of claim 1 in which said polystyrene beads comprise 3 to 9 percent by weight, and said microcrystalline cellulose comprises 90 to 96 percent by weight of said tablet.

5. The tablet of claim 1 in which said tablet also includes about 1.0 to 5.0 percent by weight of alginic acid.

6. The tablet of claim 1 in which said beads are formed of a styrene divinyl benzene polymer lattice and said quaternary ammonium exchange groups are in a chloride ionic form.

7. A water-disintegratable tablet for use in performing clinical diagnostic tests, comprising a predetermined quantity of resilient porous beads composed of a styrene divinyl benzene polymer lattice having quaternary ammonium exchange groups attached thereto and having a particle size within the range of 50 to 600 mesh, said beads being bound together by a water-swellable matrix composed essentially of microcrystalline cellulose, said beads comprising 3 to 9 percent by weight of said tablet and said microcrystalline cellulose comprising 90 to 96 percent by weight of said tablet.

8. The tablet of claim 7 in which said beads have a size within the range of 100 to 500 mesh.

9. The tablet of claim 8 in which said beads have a size within the range of 200 to 400 mesh.

10. The tablet of claim 7 in which said matrix also includes alginic acid of 1.0 to 5.0 percent by weight of said tablet.

11. The tablet of claim 7 in which said quaternary ammonium exchange groups are in a chloride ionic form.

12. A competitive binding method for measuring serum T4 comprising the steps of mixing a solution of free T4 extracted from a sample of patient's serum with a dilute buffered solution of known radioisotope-labeled T4 bound to saturated TBG, and separating the unbound T4 with an anion-exchange resin, wherein the improvement comprises providing said anion-exchange resin in the form of a tablet consisting essentially of polystyrene-based anion-exchange resin beads of 50 to 600 mesh bound together by microcrystalline cellulose, and performing said mixing and separating steps concurrently without incubating the mixed solutions prior to contact with said tablet.

13. The method of claim 12 in which there are the further steps of separating said beads from supernatant by centrifugation and decantation, and thereafter, without washing said beads, measuring the radioactivity of the unbound labeled T4 retained by said beads.

14. The method of claim 12 in which said beads are of a size within the range of 100 to 500 mesh.

15. The method of claim 12 in which said beads are of a size within the range of 200 to 400 mesh.

16. The method of claim 12 in which said polystyrene beads comprise 3 to 9 percent by weight, and said microcrystalline cellulose comprises 90 to 96 percent by weight, of said tablet.

17. The method of claim 12 in which said polystyrene-based resin beads are formed of a styrene divinyl benzene polymer lattice having quaternary ammonium exchange groups attached thereto.

18. The method of claim 17 in which said quaternary ammonium exchange groups are in chloride ionic form.

19. A competitive binding method for measuring serum T4 including the steps of equilibrating a solution of free T4 extracted from a sample of patient's serum with a dilute buffered solution of a known quantity of radioisotope-labeled T4 bound to saturated TBG, and separating the unbound T4 with an anion-exchange resin, wherein the improvement comprises performing said equilibrating and separating steps concurrently by combining said solutions and immediately thereafter introducing into said combined solutions a tablet consisting essentially of polystyrene-based anion-exchange resin beads of a size within the range of 50 to 600 mesh bound together by microcrystalline cellulose.

20. The method of claim 19 in which said beads are of a size within the range of 100 to 500 mesh.

21. The method of claim 19 in which said beads are of a size within the range of 200 to 400 mesh.

22. The method of claim 19 in which said beads comprise 3 to 9 percent by weight, and said microcrystalline cellulose comprises 90 to 96 percent by weight, of said tablet.

23. The method of claim 19 in which there are the further steps of segregating said beads and microcrystalline cellulose from supernatant by centrifugation and decantation, and thereafter, without washing said beads, measuring the radioactivity of the unbound labeled T4 retained thereby.

* * * * *